United States Patent [19]

Howarth et al.

[11] 3,948,913

[45] Apr. 6, 1976

[54] 5-NITROFURYL DERIVATIVES

[75] Inventors: Graham Arton Howarth, Knutsford; James Gainer, Tyldesley,, England

[73] Assignee: Ciba-Geigy Corporation, Ardsley, N.Y.

[22] Filed: July 3, 1974

[21] Appl. No.: 485,472

Related U.S. Application Data

[63] Continuation-in-part of Ser. No. 247,284, April 25, 1972, abandoned.

[30] Foreign Application Priority Data

Apr. 27, 1971 United Kingdom............... 11492/71
Feb. 2, 1972 United Kingdom................. 4788/72
Mar. 3, 1972 United Kingdom............... 10021/72
Mar. 3, 1972 United Kingdom............... 10022/72

[52] U.S. Cl. .................... 260/256.4 B; 260/45.8 N; 260/256.4 F; 260/310 R; 424/251; 426/532
[51] Int. Cl.$^2$...................................... C07D 487/07
[58] Field of Search................ 260/256.4 F, 256.5 B

[56] References Cited
UNITED STATES PATENTS 3,105,834  10/1963  Wei............................ 260/256.4 F
3,335,141  8/1967   Burch.......................... 260/256.4 F
3,350,397  10/1967  Burch.......................... 260/256.4 F
3,631,169  12/1971  Minami........................ 260/256.4 F
3,770,740  11/1973  Burch.......................... 260/256.4 F

OTHER PUBLICATIONS

Burch, J. Med. Chem. II (1), pp. 79–82 (1968).

*Primary Examiner*—Richard J. Gallagher
*Assistant Examiner*—Mark L. Berch
*Attorney, Agent, or Firm*—Joseph G. Kolodny; John J. Maitner; Theodore O. Groeger

[57] ABSTRACT

Compounds of the class of substituted or unsubstituted 4-amino-3-(5-nitro-2-furyl)-1H-pyrazolo[3,4-d]pyrimidine and their 5-N oxides have antimicrobial properties and are active ingredients in pharmaceutical compositions and animal feedstuff compositions, an illustrative example is 4-amino-1-methyl-3-(5-nitro-2-furyl)-1H-pyrazolo[3,4-d]pyrimidine.

7 Claims, No Drawings

NEW 5-NITROFURYL DERIVATIVES

This application is a continuation-in-part of our co-pending application Ser. No. 247,284, filed Apr. 25, 2972, now abandoned.

DETAILED DESCRIPTION

The present invention relates to nitrofuryl derivatives in particular, to derivatives of 4-amino-3-(5-nitro-2-furyl)-1H-pyrazolo[3,4-d]pyrimidine and their 5-N oxides which have antimicrobial properties. It further relates to pharmaceutical and animal feedstuff compositions containing these compounds and to methods for the treatment of mammals suffering from microbial infections, particularly of intestinal tract infections and topical skin (dermatoses and affections of the mucous membranes) infections, comprising administering to said mammals an effective amount of such compounds. The invention also provides methods for protecting organic material susceptible to microbial attack with an effective amount of a compound according to the invention.

More particularly, the present invention relates to compounds of the formula I

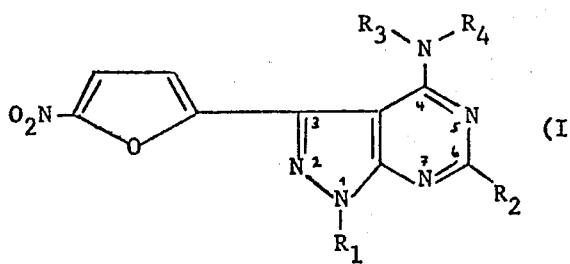

wherein
$R_1$ represents alkyl of 1 to 3 carbon atoms $R_2$ represents a hydrogen atom or alkyl of 1 to 3 carbon atoms, and $R_3$ represents a hydrogen atom, alkyl or hydroxy-alkyl of 1 to 3 carbon atoms, alkoxy-alkyl wherein the alkoxy and alkyl moieties may each contain from 1 to 3 carbon atoms, a hydroxy group while $R_4$ has the meaning given above for $R_3$ except that it may not represent a hydroxy group, or $R_3$ and $R_4$ together represent pyrrolidine, morpholine, piperidine or azepine, or as well as the 5-N oxides thereof and the acid addition salt, especially pharmaceutically acceptable acid addition salt thereof, or 5-N oxides.

The terms "lower alkyl, alkenyl, alkoxy, hydroxyalkyl, or lower-alkoxy-lower-alkyl" may be defined for the substituents $R_1$, $R_2$, $R_3$ and $R_4$ as follows:

$R_1$ and $R_2$ may be a methyl, ethyl, n-propyl or isopropyl group: and where $R_3$ is an alkyl group this may also be a methyl, ethyl, n-propyl or isopropyl group. Where $R_3$ and $R_4$ are hydroxyalkyl groups these may be hydroxymethyl, hydroxyethyl, hydroxy n-propyl or hydroxy isopropyl groups: where $R_3$ and $R_4$ are alkoxyalkyl groups these may be methoxymethyl, methoxyethyl, methoxy n-propyl, methoxy iso-propyl, ethoxymethyl, ethoxyethyl, ethoxy-n-propyl, ethoxy isopropyl, n-propoxymethyl, n-propoxyethyl, n-propoxy n-propyl, n-propoxy isopropyl, isopropoxymethyl, isopropoxyethyl, isopropoxy n-propyl or isopropoxy isopropyl groups.

Suitable organic or inorganic acids with which the compounds of formula I and their 5-N oxides may form acid addition salts, especially pharmaceutically acceptable acid addition salts, may be for example, hydrochloric, hydrobromic, sulphuric, phosphoric, methane-sulphonic, ethanedisulphonic, acetic, trichloroacetic, oxalic, succinic, maleic, fumaric, malic, tartaric, citric and mandelic acids.

In a compound of formula I or as well as in a 5-N oxide thereof, when either or both of $R_3$ and $R_4$ is hydrogen it should be noted that tautomers, for example

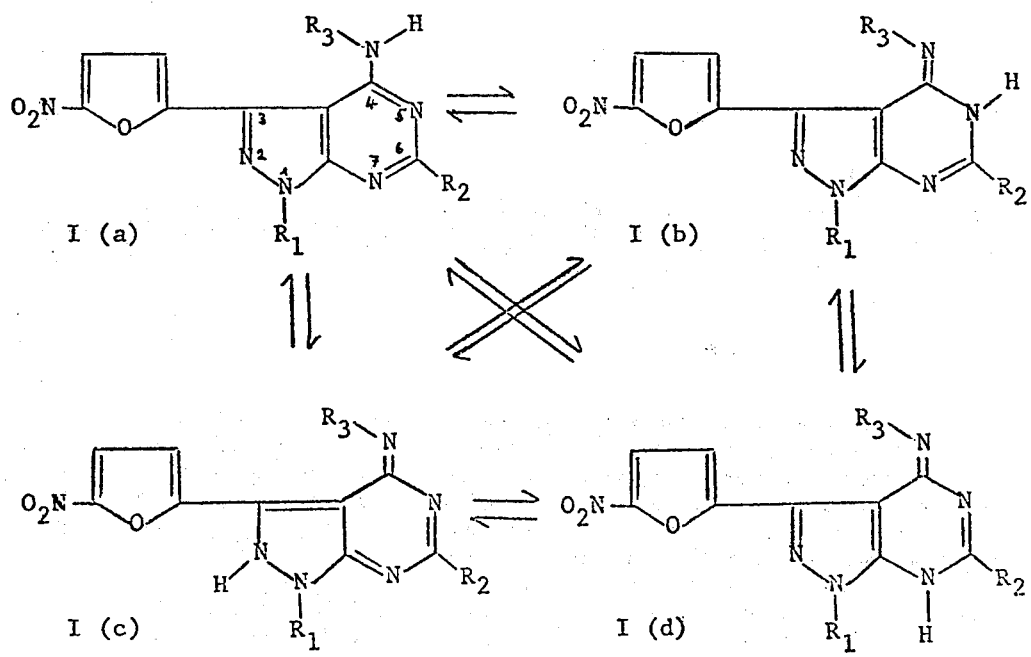

are possible in which a hydrogen atom is located on the nitrogen in ring position 2, 5 or 7.

It will be appreciated that when $R_3$ represents a hydroxy group tautomers I (b), I (c) and I (d) in the above series are 4-hydroxylamines.

The 5-N oxides can exist in an equivalent series of tautomeric forms as follows:

Preferred compounds, especially valuable in view of their antimicrobial property are compounds of general formula I wherein $R_1$ represents a low alkyl group, e.g. a methyl or ethyl group, $R_2$ represents hydrogen and $R_3$ and $R_4$ hydrogen or a low alkyl group, e.g. a methyl or ethyl group as well as their 5-N oxides and/or pharmaceutically acceptable acid addition salts thereof.

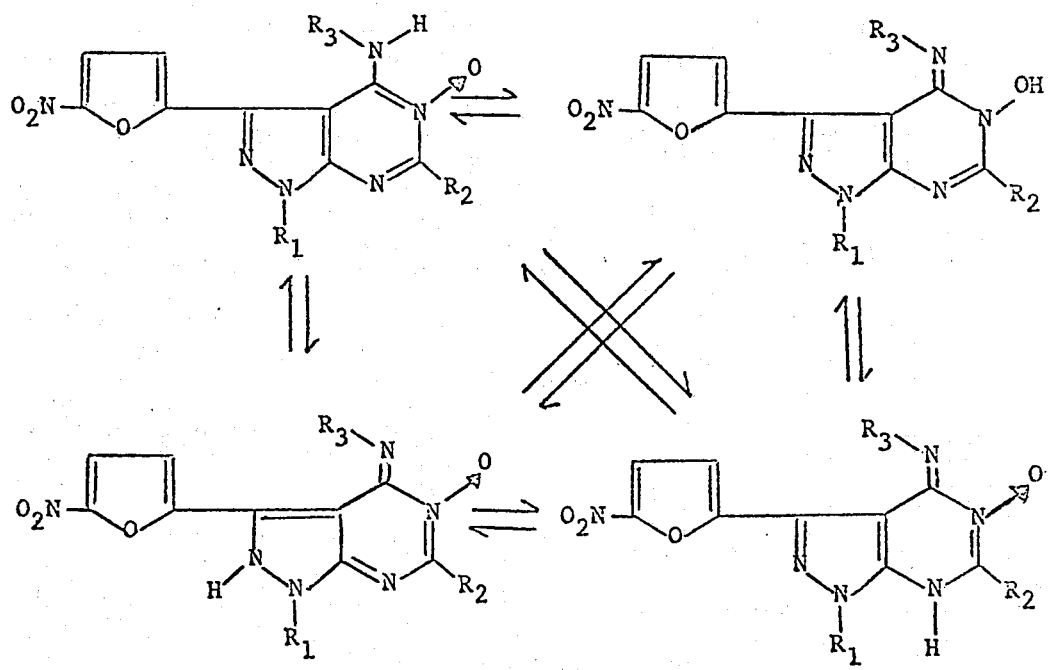

Moreover it is to be understood, when $R_3$ is hydroxy as mentioned above the N-oxide forms generated at the nitrogen atom attached to the 4-position are also contemplated in accordance with the tautomerism associated with such configuration, e.g.

The antimicrobial activity is demonstrated in a number of conventional pharmacological tests. Thus it is shown that, for example, 4-amino-1-methyl-3-(5-nitro-2-furyl)-1H-pyrazolo[3,4]pyrimidine, 4-amino-1-methyl-3-(5-nitro-2-furyl)-1H-pyrazolo[3,4-d]pyrimi-

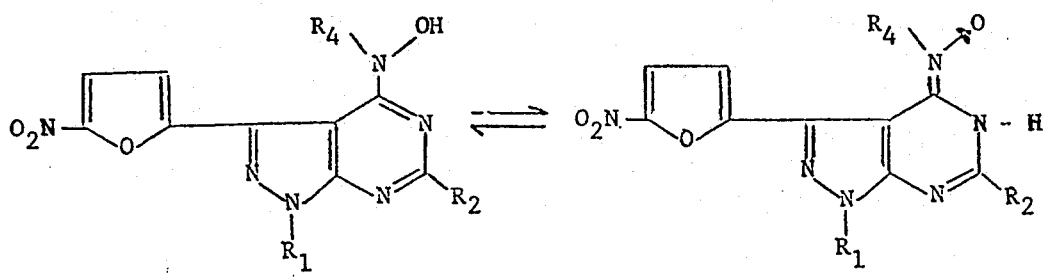

The compounds of the invention having the general formula I, their 5-N oxides as well as the salts thereof have antibacterial, antifungal, antimycoplasmal, antihelminthic, antiprotozoal, coccidiostatic, trypanocidal and antimalarial activity of value in human or veterinary medicine, and are particularly valuable in that they have a wide spectrum of activity against microbial organisms. The compounds are valuable in the treatment of infections of the intestinal tract and for topical application.

din-5-oxide and 1-methyl-4-methylamino-3-(5-nitro-2-furyl)-1H-pyrazolo[3,4-d]pyrimidine have in vitro excellent growth inhibiting effects against *Staphylococcus aureous, Escherichia coil, Klebsiella pneumonia, Salmonella typhi, Pseudomonas aeruginosa, Proteus vulgaris, Trichophyton ment., Mocrosporum canis, Sporotrichum sch., Candida alb., Asperg. fumigatus*, and others if added in amounts of about 0.1 – 10 μg/ml especially from 1 to about 10 μg/ml to the bacterial culture. It is also shown that, for example, 4-amino-1-methyl-3-(5- nitro-2-furyl)-1H-pyrazolo[3,4-d]pyrimidin-5-oxide, and 4-dimethylamino-1-methyl-3-(5-nitro-2-furyl)-1H-pyrazolo[3,4-d]pyrimidine have in vivo excellent curative effects when given per oral to mice infected with a lethal infection of *Staphylococcus aureous*.

The toxicity of the compounds of the invention as demonstrated for example in mice is of favourable low order.

For their intended internal use, for example for the treatment of intestinal tract infections, the active compounds are administered in dosages depending on the kind of infection, the species and the age, weight and particular condition of the individual being treated. In general the daily dosage upon oral application will vary from about 1 to 100 mg/kg for mammals.

The present invention also provides a first process for the preparation of compounds of formula I which comprises reacting a compound of the formula II

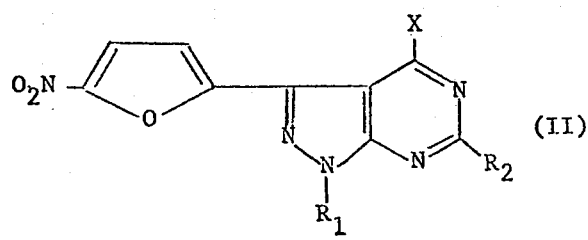

in which X is a group capable of being replaced by an amino group, with a base of general formula III $R_3R_4NH$, preferably in an organic solvent, such as ethyl acetate, which does not react under the conditions of the reaction, and at the reflux temperature of the solvent and optionally converting an obtained compound of formula I into an 5-N oxide thereof and/or optionally converting an obtained compound of formula I or a 5-N oxide thereof into an acid addition salt.

The group X may be halogen, that is chlorine, bromine or iodine, or may be a hydroxyl group esterified with a strong inorganic or organic acid, for example sulphuric acid or a sulphonic acid such as the aromatic sulphonic acids benzenesulphonic acid, 4-bromobenzenesulphonic acid or 4-toluenesulphonic acid. X may also be a free or etherified mercapto group, for example a lower alkyl mercatpo group such as methyl mercapto, or an aryl-lower alkyl mercapto group such as benzyl mercapto; it can also be a lower alkoxy group such as benzyloxy, an ammonium group, especially a tri-lower alkyl ammonium group such as trimethylammonium, a sulphonyl group, especially a lower alkyl sulphonyl group such as methylsulphonyl or a cyano group.

Compounds of formula II in which X is chlorine are novel compounds, and themselves show antimicrobial activity.

Where the compound of formula II is reacted with ammonia, this is preferably under anhydrous conditions in an inert solvent, and preferably also under pressure. Alternatively, liquid ammonia may be used: there are no temperature restrictions other than those of convenience on the carrying out of this stage.

Where the compound of formula II is reacted with a hydroxylamine of formula $R_4NHOH$, the group X reacts with the hydroxylamine with the elimination of HX to give a compound of formula I wherein $R_3$ is a hydroxy group. The solvent preferably used is methyl alcohol. The conversion of compound of formula I into a 5-N oxide is performed by oxidising a compound of formula I with a peroxy compound. For instance the reaction may be carried out using hydrogen peroxide in a suitable solvent such as glacial acetic acid, or using a suitable organic per acid such as peracetic acid as both reagent and solvent, or using tertiary amyl hydroperoxide and molybdenum pentachloride.

Compounds of formula II in which X is halogen may be prepared by treating a compound of the general formula IV

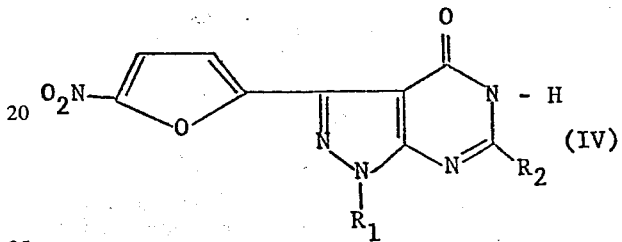

with a chlorinating or brominating agent optionally in the presence of a proton acceptor. Preferably the halogenating agent will be a phosphorus-containing agent, of the type conventionally used in this kind of reaction, and then it is desirable that a proton acceptor should be present.

Preferably the chlorination or bromination of the compound of formula IV is carried out in the presence of dimethyl aniline as proton-acceptor using phosphorus oxychloride as halogenating agent; other halogenating agents such as phosphorus pentachloride, phosphorus oxybromide or phosphorus pentabromide could be used. A convenient temperature range for this stage is from room temperature to the reflux temperature of the reaction mixture.

The starting materials for this process compounds of formula IV are prepared, for instance, by treating a compound of the general formula V

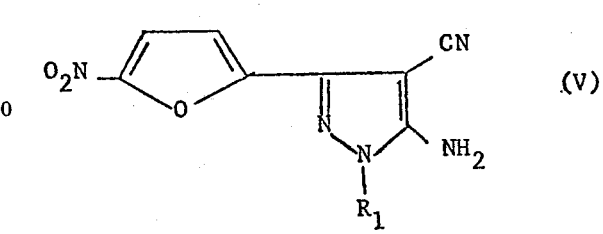

with an acid anhydride $(R_2CO)_2O$ or acid chloride $R_2COCl$ in the presence of an acid or basic catalyst, to form an intermediate VI

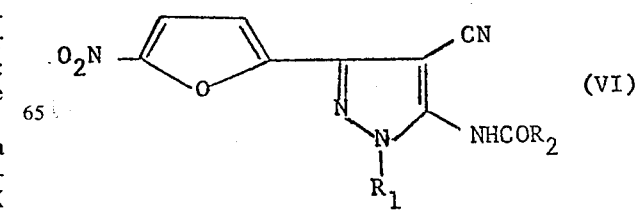

and subsequently cyclising this intermediate with or without preliminary isolation. Compounds of formula V are known compounds and described in the South African Pat. No. 70/1303.

The invention also provides a second process for the preparation of those compounds of formula I in which $R_2$ and $R_3$ are both hydrogen, and in which $R_4$ is hydrogen, an alkyl or hydroxy alkyl group, an alkenyl group, or an alkoxyalkyl group, which comprises reacting a compound of the formula VII

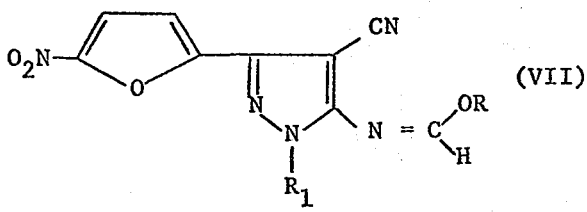

in which $R_1$ is an alkyl group with a base $R_4NH_2$ and optionally converting an obtained compound of formula I into a 5-N oxide thereof and/or optionally converting an obtained compound of formula I or a 5-N oxide thereof into an acid addition salt. Preferably this reaction is effected by treating the compound of formula VII with an aqueous alcoholic solution of the base at a temperature between room temperature and the reflux temperature of the solution. When $R_4$ is hydrogen, the base used, may be ammonia or a compound such as hexamine, which will yield ammonia under the conditions of the reactions.

Compounds of formula VII are known compounds; they may be prepared by a simple series of steps from a nitrofurylnitrilimine which in one of its canonical forms may be represented by the formula VIII

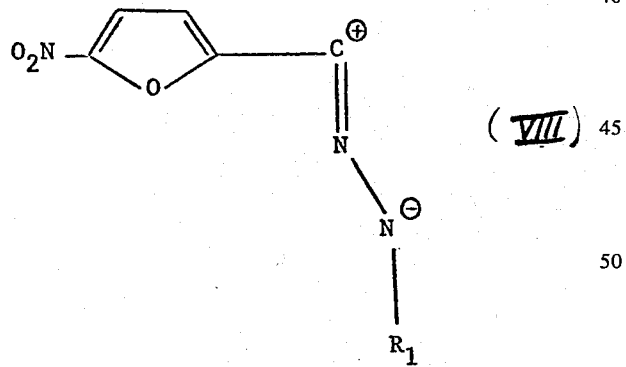

where $R_1$ has its previous significance. Reaction of this compound with malononitrile, as described in South African Pat. No. 70/1303, yields a nitrofurylpyrazole derivative of the general formula V

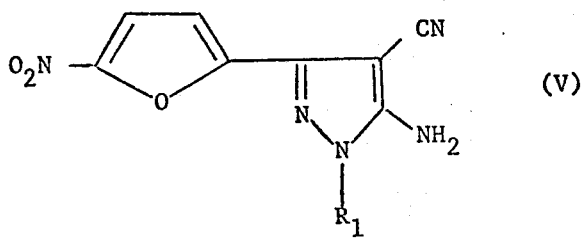

Compounds of formula VII may be derived from compounds of formula V by reacting the latter with a reagent $R_2C(OR)_3$ and removing the alkanol produced from the reaction mixture by chemical or physical means, as the reaction proceeds. The removal of alkanol as the reaction proceeds may be done by chemical means, for example by conducting the reaction in the presence of a carboxylic acid anhydride, such as acetic anhydride, or by physical means, for example by distilling off the alkanol as formed. If desired, the reaction may be carried out in the presence of an anhydrous non-reactive solvent.

The present invention also provides a process for preparing a compound of formula I in which $R_1$ is an alkyl group and $R_2$, $R_3$ and $R_4$ are all hydrogen which comprises reacting a compound of formula V

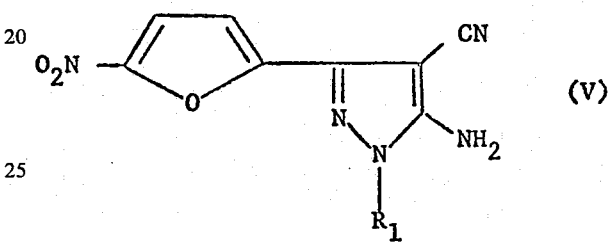

with formamide at reflux temperature.

The present invention also provides a process for preparing 5-N oxides of compounds of formula I in which $R_1$ is an alkyl group and $R_2$, $R_3$ and $R_4$ are hydrogen which comprises reacting a compound of formula VII

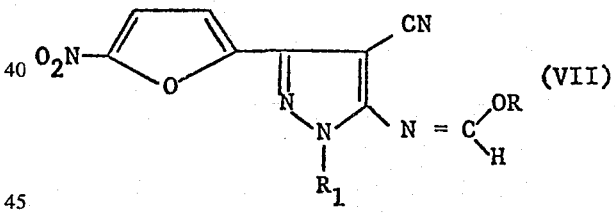

wherein R and $R_1$ are low alkyl groups with hydroxylamine in a suitable solvent such as aqueous ethanol.

According to their antimicrobial activity the compounds of formula I, their 5-N oxides and their acid addition salts may be used to protect a high molecular weight hydrophobic or other organic material susceptible to bacterial or other microbial deterioration by contacting the organic material with, impregnating in or otherwise treating with, the compounds in amounts up to about 5 % by weight. The compounds also find application as growth-promoting additives to animal feedstuffs, to which they may be added in proportion of from 5 to 500 parts per million.

Accordingly, the invention also provides a therapeutic composition comprising an antimicrobially effective proportion of a compound of formula I, or their 5-N oxides or pharmaceutically acceptable acid addition salts thereof and a pharmacologically acceptable solid carrier or liquid diluent.

The pharmaceutical compositions according to the invention contain at least one compound of the general formula I, or their 5-N oxides or a pharmaceutically acceptable acid addition salt thereof as active substance together with a conventional pharmaceutical carrier. The type of carrier actually used depends to a great extent on the intended application; for external use, for example in disinfecting healthy skin, disinfecting wounds and in treating dermatoses and affections of the mucous membranes caused by bacteria or fungi, ointments, powders and tinctures are used in particular. The ointment bases may be anhydrous, for instance they can consist of mixtures of wool fat and soft paraffin, or they can consist of aqueous emulsions in which the active substance is suspended. Suitable carriers for powders are, for instance, rice starch and other starches; the bulk weight of the carriers may be made lighter, if desired, for example by adding highly despersed silicic acid, or may be made heavier by adding talcum. The tinctures may contain at least one active ingredient of the formula I, or 5-N oxides thereof or an acid addition salt thereof in aqueous ethanol, in particular 45 % to 75 % ethanol, to which 10 % to 20 % of glycerol may be added, if desired. Solutions prepared from polyethylene glycol and other conventional solubility promoters, and also, optionally from emulsifying agents, may be used with particular advantage in disinfecting healthy skin. The content of active ingredient in pharmaceutical compositions for external application is preferably in the range of from 0,1 % to 5 %.

Gargles or concentrates for their preparation, and tablets for slow dissolution in the mouth, are suitable for the disinfection of the mouth and throat. The former are preferably prepared from alcoholic solutions containing 1 % to 5 % of active substance to which glycerol or flavourings may be added. Lozenges, that is solid dosage units, preferably have a relatively high content of sugar or similar substances and a relatively low content of active substance, for instance 0,2 % to 20 % by weight, as well as the usual conventional additives such as binding agents and flavourings.

Solid dosage units, in particular tablets, dragées (sugar coated tablets) and capsules, are convenient for use in intestinal disinfection. These units preferably contain from 10 % to 90 % of the compound of the general formula I, their 5-N oxides or an acid addition salt thereof to enable the administration of daily doses of from 0,1 to 2,5 grams to adults, or of suitably reduced doses to children to be made. Tablets and dragée cores are produced by combining the compounds of the general formula I, their 5-N oxides or a pharmaceutically acceptable acid addition salt thereof with solid, pulverulent carriers such as lactose, saccharose, sorbitol, maize starch, potato starch or amylopectin, cellulose derivatives or gelatines, preferably with the addition of lubricants such as magnesium or calcium stearate or polyethylene glycols of suitable molecular weight. Dragée cores may then be coated, for example with concentrated sugar solutions which can also contain gum arabic, talcum and/or titanium dioxide, or they may be coated with a lacquer dissolved in volatile organic solvents or mixtures of solvents. Dyestuffs can be added to these coatings, for instance to differentiate between varying dosages. Soft gelatine capsules and other closed capsules consist, for example, of a mixture of gelatines and glycerol and may contain, for example, mixtures of the compound of formula I, their 5-N oxides or a pharmaceutically acceptable acid addition salt thereof with polyethylene glycol. Hard gelatine capsules contain, for example, granulates of an active substance with solid pulverulent carriers, for instance lactose, saccharose, sorbitol, mannitol, starches (such as potata starch, maize starch or amylopectin), cellulose derivatives of gelatines, and magnesium stearate or stearic acid.

In all forms for administration compounds of the general formula I, their 5-N oxides or an acid addition salt thereof can be present as sole active ingredients or they can also be combined with other known pharmacologically active, and especially antibacterial and/or antimycotically or other antimicrobially active substances, for example to broaden the range of application. They can be combined for example, with 5,7-dichloro-2-methyl-8-quinolinol or other derivatives of 8-quinolinol or other derivatives of 8-quinolinol, with sulfamerazine or sulfafurazole or other derivatives of sulfanilamide, with chloramphenicol or tetracycline or other antibiotics, with 3,4',5-tribromosalicylanilide or other halogenated salicylanilides, with halogenated carbanilides, with halogenated benzoxazoles or benzoxazolones, with polychloro-hydroxy-diphenylmethanes, with halogen-dihydroxy-diphenyl sulphides, with 4,4'-dichloro-2-hydroxy-diphenylether or 2,4,4'-trichloro-2-hydroxydiphenylether or other polyhalogenhydroxydiphenylethers, or with bactericidal quaternary compounds or with certain dithiocarbamic acid derivatives such as tetramethylthiuram disulphide or with other nitrofurans. Also, carriers which themselves have favourable pharmacological properties may be used, for instance sulphur as a powder base or zinc stearate as a component of ointment bases.

The invention also provides a method of protecting an organic material susceptible to bacterial or other microbial attack which comprises treating the material with a compound of formula I, their 5-N oxides or an acid addition salt thereof. The organic material may be a natural or synthetic polymeric material, a proteinaceous or carbohydrate substance, or a natural or synthetic fibre or textile material formed therefrom.

The invention also provides an animal feedstuff composition comprising a compound of formula I, their 5-N oxides or an acid addition salt thereof in an amount sufficient to promote the growth of the animal fed with the composition.

Some Examples will now be given, all parts and percentages being by weight unless otherwise stated. The temperatures are given in centigrade.

EXAMPLE 1

A mixture of 20.0 grams of 4-cyano-5-ethoxymethyleneamino-1-methyl-3-(5-nitro-2-furyl)-pyrazole, 200 milliliters of ethanol and 100 milliliters of concentrated aqueous ammonia solution (S.G., 0.88) was heated at reflux for 1 hour and cooled. The crystalline solid precipitated was collected, washed with water and dried. Recrystallisation from dimethylformamide gave 4-amino-1-methyl-3-(5-nitro-2-furyl)-1H-pyrazolo[3,4-d]pyrimidine having decomposition point 305°C.

On characterisation by means of proton NMR spectrum (trifluoracetic acid), the following values were observed:

$\delta$ (ppm). 8.75 (2H,$s$,exchangeable), 8.70 (1H,$s$), 7.60 (1H,$d$), 7.44 (1H,$d$), 4.26 (3H,$s$).

EXAMPLE 2

The procedure described in Example 1 was repeated using 4-cyano-5-(1-ethoxyethylideneamino)-1-methyl-3-(5-nitro-2-furyl)-pyrazole as starting material instead of 4-cyano-5-ethoxymethyleneamino-1-methyl-3-(5-nitro-2-furyl)-pyrazole, the reaction conditions being the same.

The product was 4-amino-1,6-dimethyl-3-(5-nitro-2-furyl)-1H-pyrazolo[3,4-d]pyrimidine, having decomposition point > 300°C.

On characterisation by means of proton NMR spectrum (trifluoroacetic acid), the following values were observed:

δ (ppm). 8.51 (2H,s, exchangeable), 7.65 (1H,d), 7.45 (1H,d), 4.23 (3H,s), 2.83 3H,s).

EXAMPLE 3 a. To a mixture of 5.0 grams of 1-methyl-3-(5-nitro-2-furyl)-1H-pyrazolo[3,4-d]pyrimidin-4(5H)one and 100 milliliters of phosphorus oxychloride was slowly added 48 grams of N,N-dimethylaniline. The mixture was heated under reflux for 2 hours, cooled and carefully added to 1 kilogram of crushed ice. The crystalline product was collected, washed with ether and dried. Recrystallisation from ethyl acetate gave 4-chloro-1-methyl-3-(5-nitro-2-furyl)-1H-pyrazolo[3,4-d]pyrimidine having melting point 195°C.

b. A mixture of 1.0 grams of 4-chloro-1-methyl-3-(5-nitro-2-furyl)-1H-pyrazolo[3,4-d]pyrimidine and a solution of 100 milliliters of dry ethanol saturated at room temperature with ammonia gas, was heated in a sealed stainless steel tube at a bath temperature of 130°C. and 7 atmospheres pressure for 3 hours, and cooled. The crystalline product was collected washed with water and dried. Recrystallisation from dimethylformamide gave 4-amino-1-methyl-3-(5-nitro-2-furyl)-1H-pyrazole[3,4-d]pyrimidine having decomposition point 305°C. identical with the product obtained in Example 1.

EXAMPLE 4 a. The procedure described in Example 3a was repeated using 1,6-dimethyl-3-(5-nitro-2-furyl-1H-pyrazolo[3,4-d]pyrimidin-4-(5H)-one as starting material instead of 1-methyl-3-(5-nitro-2-furyl)-1H-pyrazolo[3,4-d]pyrimidin-4 (5H)-one, the reaction conditions being the same. The crystalline product was collected, washed with water and dried. Recrystallisation from ethyl acetate gave 4-chloro-1,6-dimethyl-3-(5-nitro-2-furyl)-1H-pyrazolo[3,4-d]pyrimidine having melting point 212°C.

b. The procedure described in Example 3b was repeated using 4-chloro-1,6-dimethyl-3-(5-nitro-2-furyl)-1H-pyrazolo[3,4]pyrimidine as starting material instead of 4-chloro-1-methyl-3-(5-nitro-2-furyl)-1H-pyrazolo[3,4-d]pyrimidine, the reaction conditions being the same. The crystalline product was collected, washed with water and dried. Recrystallisation from dimethyl formamide gave 4-amino-1,6-dimethyl-3-(5-nitro-2-furyl)-1H-pyrazolo[3,4-d]pyrimidine having decomposition point > 300°C. identical with the product obtained in Example 2.

EXAMPLE 5 a. The procedure described in Example 3a was repeated using 6-ethyl-1-methyl-3-(5-nitro-2-furyl)-1H-pyrazolo[3,4-d]pyrimidin-4 (5H)-one as starting material instead of 1-methyl-3-(5-nitro-2-furyl)-1H-pyrazolo[3,4-d]pyrimidin-4 (5H)-one, the reaction conditions being the same. The crystalline product was collected, washed with water and dried. Recrystallisation from ethyl acetate gave 4-chloro-6-ethyl-1-methyl-3-(5-nitro-2-furyl)-1H-pyrazolo[3,4-d]pyrimidine having melting point 165°C.

b. The procedure described in Example 3b was repeated using 4-chloro-6-ethyl-1-methyl-3-(5-nitro-2-furyl)-1H-pyrazolo[3,4-d]pyrimidine as starting material instead of 4-chloro-1-methyl-3-(5-nitro-2-furyl)-1H-pyrazolo[3,4-d]pyrimidine, the reaction conditions being the same. The crystalline product was recrystallised from dimethyl formamide to give 4-amino-6-ethyl-1-methyl-3-(5-nitro-2-furyl)-1H-pyrazolo[3,4-d]pyrimidine, having decomposition point 294°C.

On characterisation by means of proton NMR spectrum (trifluoroacetic acid), the following values were observed.

δ (ppm). 8.50 (2H,s exchangeable), 7.60 (1H,d), 7.50 (1H,d), 4-28 (3H,s), 3.08 (2H,q), 1.51 (3H,t).

EXAMPLE 6 a. The procedure described in Example 3a was repeated using 6-isopropyl-1-methyl-3-(5-nitro-2-furyl)-1H-pyrazolo[3,4-d]pyrimidin-4(5H)-one as starting material instead of 1-methyl-3-(5-nitro-2-furyl)-1H-pyrazolo[3,4-d]pyrimidin-4(5H)-one, the reaction conditions being the same. The crystalline product obtained was collected, washed with 60°–80°C petroleum ether and dried. Recrystallisation from a 1:3 mixture of toluene and 60°–80°C petroleum ether (v/v) gave 4-chloro-6-isopropyl-1-methyl-3-(5-nitro-2-furyl)-1H-pyrazolo[3,4-d]pyrimidine having melting point 112°C.

b. The procedure described in Example 3b was repeated using 4-chloro-6-isopropyl-1-methyl-3-(5-nitro-2-furyl)-1H-pyrazolo[3,4-d]pyrimidine as starting material instead of 4-chloro-1-methyl-3-(5-nitro-2-furyl)-1H-pyrazolo[3,4-d]pyrimidine, the reaction conditions being the same. The crystalline product was recrystalized from dimethylformamide to give 4-amino-6-isopropyl-1-methyl-3-(5-nitro-2-furyl)-1H-pyrazolo[3,4-d]pyrimidine having decomposition point 230°C.

On characterisation by means of proton NMR spectrum (trifluoroacetic acid), the following values were observed:

δ (ppm). 8.47 (2H,s exchangeable), 7.63 (1H,d), 7.47 (1H,d), 4.27 (3H,s), 3.11 (1H, septet), 1.51 (6H,d).

EXAMPLE 7

A mixture of 5.0 grams of 5-amino-4-cyano-1-methyl-3-(5-nitro-2-furyl)-pyrazole and 10 milliliters of formamide was heated under vigorous reflux for 30 minutes and cooled.

The solid product was collected and shown by means of thin layer chromatography to contain 4-amino-1-methyl-3-(5-nitro-2-furyl)-1H-pyrazolo[3,4-d]pyrimidine identical to the product obtained in Example 1.

EXAMPLE 8 a. To a mixture of 5.0 grams of 1-methyl-3-(5-nitro-2-furyl)-1H-pyrazolo[3,4-d]pyrimidin-4(5H)-one and 100 milliliters of phosphorus oxychloride were slowly added 48 grams of N,N-dimethylaniline. The mixture was heated under reflux for 2 hours, cooled and carefully added to 1 kilogram of crushed ice. The crystalline product was collected, washed with ether and dried. Recrystallisation from ethyl acetate gave 4-chloro-1-methyl-3-(5-nitro-2-furyl)-1H-pyrazolo[3,4-d]pyrimidine having melting point 195°C.

b. A mixture of 10.0 grams of 4-chloro-1-methyl-3-(5-nitro-2-furyl)-1H-pyrazolo[3,4-d]pyrimidine, 6.0 grams of dimethylamine and 600 milliliters of ethyl acetate was heated at reflux for 30 minutes, cooled and filtered. The filtrate was extracted with three 100 milliliters portions of water. The organic layer was dried over anhydrous magnesium sulphate and evaporated down to dryness. The crystalline product was collected, washed with ethanol and dried. Recrystallisation from ethyl acetate gave 4-dimethylamino-1-methyl-3-(5-nitro-2-furyl)-1H-pyrazolo[3,4-d]pyrimidine having melting point 161°C.

EXAMPLE 9

The procedure described in Example 8 was carried out using an equivalent weight of pyrrolidine as starting material instead of dimethylamine, the reaction conditions being the same.

The product was 1-methyl-3-(5-nitro-2-furyl)-4-pyrrolidino-1H-pyrazolo[3,4-d]pyrimidine, m.p. 185°C.

EXAMPLE 10

The procedure described in Example 8 was carried out using an equivalent weight of piperidine as starting material instead of dimethylamine, the reaction conditions being the same.

The product was 1-methyl-3-(5-nitro-2-furyl)-4-piperidino-1H-pyrazolo[3,4-d]pyrimidine, m.p. 184°C.

EXAMPLE 11

The procedure described in Example 8 was carried out using an equivalent weight of morpholine as starting material instead of dimethylamine, the reaction conditions being the same.

The product was 1-methyl-4-morpholino-3-(5-nitro-2-furyl)-1H-pyrazolo[3,4-d]pyrimidine, m.p. 211°C.

EXAMPLE 12

The procedure described in Example 8 was carried out using an equivalent weight of diethanolamine as starting material instead of dimethylamine, the reaction conditions being the same.

The product was 4-(di-2-hydroxyethylamino)-1-methyl-3-(5-nitro-2-furyl)-1H-pyrazolo[3,4-d]pyrimidine, having melting point 168°C.

EXAMPLE 13

A mixture of 10.0 grams of 4-cyano-5-ethoxymethyleneamino-1-methyl-3-(5-nitro-2-furyl)-pyrazole, and 100 milliliters of a 33 % solution of methylamine in ethanol was heated at reflux for 30 minutes and cooled. The crystalline solid precipitated was collected, washed with ether and dried. Recrystallisation from dimethylformamide gave 4-methylamino-1-methyl-3-(5-nitro-2-furyl)-1H-pyrazolo[3,4-d]pyrimidine, having melting point 280°C.

EXAMPLE 14

The procedure described in Example 13 was carried out using an equivalent weight of ethylamine as starting material instead of methylamine, the reaction conditions being the same.

The product was 4-ethylamino-1-methyl-3-(5-nitro-2-furyl)-1H-pyrazolo[3,4-d]pyrimidine, having melting point 240°C.

EXAMPLE 15

The procedure described in Example 13 was carried out using an equivalent weight of ethanolamine as starting material instead of methylamine, the reaction conditions being the same.

The product was 4-(2-hydroxyethylamino)-1-methyl-3-(5-nitro-2-furyl)-1H-pyrazolo[3,4-d]pyrimidine, having melting point 212°C.

EXAMPLE 16

The procedure described in Example 13 was carried out using an equivalent weight of 3-methoxy-propylamine as starting material instead of methylamine, the reaction conditions being the same.

The product was 4-(3-methoxypropylamino)-1-methyl-3-(5-nitro-2-furyl)-1H-pyrazolo[3,4-d]pyrimidine, having melting point 173°C.

EXAMPLE 17

The product described in Example 13 was carried out using an equivalent weight of allylamine as starting material instead of methylamine, the reaction conditions being the same.

The product was 4-allylamino-1-methyl-3-(5-nitro-2-furyl)-1H-pyrazolo[3,4-d]pyrimidine, having melting point 177°C.

EXAMPLE 18

The procedure described in Example 8 was carried out using an equivalent weight of methylamine as the starting material instead of dimethylamine, the reaction conditions being the same.

The product was 4-methylamino-1-methyl-3-(5-nitro-2-furyl)-1H-pyrazolo[3,4-d]pyrimidine having melting point 280°C., identical to the product obtained in Example 13.

EXAMPLE 19 a. 5.0 grams of 4-chloro-1-methyl-3-(5-nitro-2-furyl)-1H-pyrazolo[3,4-d]pyrimidine was added in small portions to a solution of 10 grams of methyl mercaptan, dissolved in a mixture of 5 grams of potassium hydroxide and 30 milliliters of methanol. The mixture was heated at reflux for 30 minutes and cooled. The crystalline product formed was collected washed with water and dried. Recrystallisation gave 1-methyl-4-methyl-mercapto-3-(5-nitro-2-furyl)-1H-pyrazolo[3,4-d]pyrimidine.

b. A mixture of 3.0 grams of 1-methyl-4-methyl-mercapto-3-(5-nitro-2-furyl)-1H-pyrazolo[3,4-d]pyrimidine, 50 milliliters of a 33 % solution of methylamine in ethanol and 20 milliliters of ethyl acetate was heated at reflux for 1 hour and cooled. The crystalline product formed was collected, washed with ethanol and dried. Recrystallisation from ethyl acetate gave 4-methylamino-1-methyl-3-(5-nitro-2-furyl)-1H-pyrazolo[3,4-d]pyrimidine having melting point 280°C. identical to the product obtained in Example 13.

EXAMPLE 20

A mixture of 2.0 grams of 4-amino-1-methyl-3-(5-nitro-2-furyl)-1H-pyrazolo[3,4-d]pyrimidine dissolved in 100 milliliters of glacial acetic acid and 10 milliliters of 30 % w/v hydrogen peroxide solution (100 volumes) was allowed to stand at room temperature for 3 days. The reaction mixture was evaporated to dryness and the solid product was collected, washed with acetic acid and dried. Recrystallisation from water gave 4-amino-1-methyl-3-(5-nitro-2-furyl)-1H-pyrazolo[3,4-d]pyrimidin-5-oxide, having melting point 285°C.

On characterisation by means of proton NMR spectrum (trifluoracetic acid) the following values were observed:

δ (ppm) 8.53 (1H, s exchangeable); 8.25 (1H, s); 8.00 (1H, s exchangeable); 7.17 (1H, d); 6.95 (1H, d); 3.76 (3H, s).

The infra-red spectrum shows the following maximum absorptions;
(nujol mull) 3490, 1640, 1572cm$^{-1}$

EXAMPLE 21

A mixture of 14.4 grams of 4-cyano-5-ethoxymethylene amino-1-methyl-3-(5-nitro-2-furyl)-pyrazole, 3.5 grams of hydroxylamine hydrochloride, 150 milliliters of ethanol and a solution containing 2.0 grams of sodium hydroxide dissolved in 10 milliliters of water was heated at reflux for 1 hour and cooled. The crystalline product was filtered, washed with ethanol and dried. Recrystallisation from water gave 4-amino-1-methyl-3-(5-nitro-2-furyl)-1H-pyrazolo[3,4-d]pyrimidin-5-oxide having melting point 285°C; melting point, infra-red and proton NMR spectra being identical with the product obtained in Example 20.

EXAMPLE 22 a. A solution containing 0.7 grams of anhydrous hydroxylamine in 50 milliliters of methanol was added to a solution containing 1.4 grams of 4-chloro-1-methyl-3-(5-nitro-2-furyl)-1H-pyrazolo[3,4-d]pyrimidine dissolved in 600 milliliters of ethanol, at a temperature of 30°C. and the mixture was allowed to stand for 30 minutes at room temperature. The mixture was gently heated at reflux for a further 15 minutes and cooled. The crystalline product was washed with ether and dried. Recrystallisation from dimethylformamide gave 4-hydroxyamino-1-methyl-3-(5-nitro-2-furyl)-1H-pyrazolo[3,4-d]pyrimidine, having melting point 294°C.

On characterisation by means of NMR spectrum (trifluoracetic acid) the following values were observed:

δ (ppm) 8.73 (1H, s); 7.53 (1H, d); 7.36 (1H, d); 4.30 (3H, s);

The infra-red spectrum showed the following maximum absorptions:
(nujol mull) 3300, 1655, 1595 cm$^{-1}$ b. To a mixture of 5.0 grams of 1-methyl-3-(5-nitro-2-furyl)-1H-pyrazolo[3,4-d]pyrimidin-4(5H)-one and 100 milliliters of phosphorus oxychloride were slowly added 48 grams of N,N-dimethylaniline. The mixture was heated under reflux for 2 hours, cooled and carefully added to 1 kilogram of crushed ice. The crystalline product was collected, washed with ether and dried. Recrystallisation from ethyl acetate gave 4-chloro-1-methyl-3-(5-nitro-2-furyl)-1H-pyrazolo[3,4-d]pyrimidine having melting point 195°C.

EXAMPLE 23

Preparation of Tablets 100 g of 4-amino-1-methyl-3-(5-nitro-2-furyl)-1H-pyrazolo[3,4-d]pyrimidin-5-oxide are mixed with 60.0 g of maize starch and 35.0 g of lactose, the mixture is moistened with a solution of 5.0 g of gelatin and 3.0 g of glycerol in 70.0 g of water and granulated through a sieve. The granulate is mixed with a mixture of 15.0 g of talcum, 10.0 g of maize starch and 2.0 g of magnesium stearate. The resulting mixture is pressed into 1,000 tablets, each containing 100 mg of active substance. If desired, the tablets can be grooved for better adaption of the dosage.

EXAMPLE 24

Preparation of Dragées

| | Composition | for 1,000 dragées |
|---|---|---|
| I | 4-amino-1-methyl-3-(5-nitro-2-furyl)-1H-pyrazolo[3,4-d]pyrimidine | 100.0 g |
| | Maize starch | 27.0 g |
| | Gelatin | 8.0 g |
| II | Glycerol | 2.0 g |
| | Distilled water q.s. ad 100 ml | |
| | Maize starch | 10.0 g |
| III | Talcum | 7.0 g |
| | Magnesium stearate | 1.0 g |
| | | 155.0 g |
| IV | White dragée coating | |
| | Shellac | 2.0 g |
| | Sugar | 50.0 g |
| | Talcum | 38.0 g |
| | Gum arabic | 7.4 g |
| | Colloidal silicon dioxide | 2.2 g |
| | Titanium dioxide | 0.4 g |

Composition I is granulated in the heat with composition II through a sieve of 1.2 mm mesh diameter. The dried granulate is mixed with composition III and the resulting mixture is pressed into 1,00 dragée cores. These are then coated with composition IV and dried. The dragées obtained weigh 255.0 mg and contain 100 mg of active substance.

EXAMPLE 25

Preparation of a Syrup

| Composition | for 1 liter |
|---|---|
| 1-methyl-amino-3-(5-nitro-2-furyl)-1H-pyrazolo[3,4-d]pyrimidine | 100.0 g |
| Colloidal silicone dioxide | 13.0 g |
| p-Hydroxybenzoic acid methyl ester | 1.4 g |
| p-Hydroxybenzoic acid propyl ester | 0.6 g |
| | 115.0 g |
| | 115.0 g |
| Citric acid | 1.0 g |
| Sodium cyclamate | 5.0 g |
| Distilled water | 610.0 g |
| Glycerol | 100.0 g |
| Sodium carboxymethyl cellulose | 4.0 g |
| Sugar | 320.0 g |
| | 1155.0 g |

The active substance and the colloidal silicon dioxide are passed through a sieve of 1.2 mm mesh diameter (I).

The p-hydroxybenzoic acid esters, the citric acid and the sodium cyclamate are dissolved in the given amount of boiling distilled water, the glycerol is then added to this solution (II). The sodium carboxymethyl cellulose and the sugar are thoroughly mixed (III).

Composition III is then added at 75°C to Solution II under stirring until complete dissolution of III. The viscous, slightly turbid liquid is cooled to room temperature, filtered, if necessary, and mixed with composition I. Water is added to the resulting mixture up to the prescribed weight of 1,155.0 g and the syrup obtained is homogenized.

We claim:
1. A compound of formula I

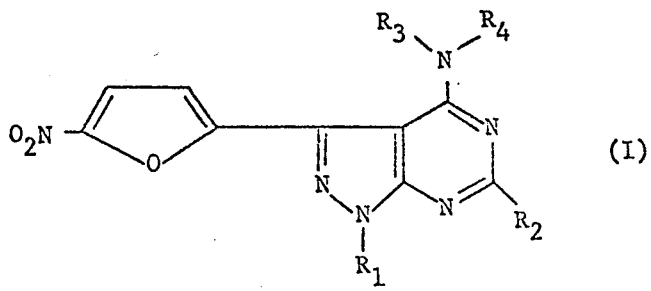

(I)

wherein
$R_1$ represents alkyl of 1 to 3 carbon atoms,
$R_2$ represents a hydrogen atom or alkyl of 1 to 3 carbon atoms, and
$R_3$ represents a hydrogen atom, alkyl or hydroxy-alkyl of 1 to 3 carbon atoms, alkoxyalkyl wherein the alkoxy and alkyl moieties may each have from 1 to 3 carbon atoms or a hydroxy group, while
$R_4$ has the meaning given above for $R_3$ except that it may not represent a hydroxy group, or
$R_3$ and $R_4$ together represent pyrrolidine, morpholine, piperidine or azepine, as well as the 5-N oxides of said compounds and/or pharmaceutically acceptable acid addition salt thereof.

2. A compound of formula I
wherein
$R_1$ represents alkyl of 1 to 3 carbon atoms
$R_2$ hydrogen, and
$R_3$ and $R_4$ hydrogen or alkyl of 1 to 3 carbon atoms as well as the 5-N oxides thereof and/or pharmaceutically acceptable acid addition salt thereof.

3. A compound of formula I
wherein
$R_1$ represents methyl or ethyl,
$R_2$ hydrogen, and
$R_3$ and $R_4$ hydrogen or methyl or ethyl as well as the 5-N oxides thereof and/or pharmaceutically acceptable acid addition salt thereof.

4. 4-Amino-1-methyl-3-(5-nitro-2-furyl)-1H-pyrazolo[3,4-d]pyrimidin-5-oxide as well as its pharmaceutically acceptable acid addition salts thereof.

5. 4-Amino-1-methyl-3-(5-nitro-2-furyl)-1H-pyrazolo[3,4-d]pyrimidine as well as its pharmaceutically acceptable acid addition salts thereof.

6. 1-Methyl-4-methylamino-3-(5-nitro-2-furyl)-1H-pyrazolo[3,4-d]pyrimidine as well as its pharmaceutically acceptable acid addition salts thereof.

7. 4-Dimethylamino-1-methyl-3-(5-nitro-2-furyl)-1H-pyrazolo[3,4-d]pyrimidine as well as its pharmaceutically acceptable acid addition salts thereof.

* * * * *